(12) United States Patent
Seward et al.

(10) Patent No.: US 6,872,433 B2
(45) Date of Patent: Mar. 29, 2005

(54) SHAPE MEMORY ALLOY/SHAPE MEMORY POLYMER TOOLS

(75) Inventors: Kirk P. Seward, Pleasanton, CA (US); Peter A. Krulevitch, Pleasanton, CA (US)

(73) Assignee: The Regents of the University of California, Oakland, CA (US)

(*) Notice: Subject to any disclaimer, the term of this patent is extended or adjusted under 35 U.S.C. 154(b) by 29 days.

(21) Appl. No.: 09/819,111

(22) Filed: Mar. 27, 2001

(65) Prior Publication Data

US 2002/0142119 A1 Oct. 3, 2002

(51) Int. Cl.⁷ .............................................. B29D 23/00
(52) U.S. Cl. .................. 428/36.9; 428/35.7; 428/36.91; 428/36.92; 428/913; 606/198; 606/209; 606/281; 604/317; 604/540; 623/1.11; 623/1.15; 623/1.17; 623/1.2
(58) Field of Search ................................ 606/209, 198, 606/281; 428/36.9, 36.91, 36.92, 35.7, 913; 604/317, 540; 623/1.11, 1.15, 1.17, 1.2

(56) References Cited

U.S. PATENT DOCUMENTS

| | | | |
|---|---|---|---|
| 5,405,337 A | 4/1995 | Maynard | 604/281 |
| 5,674,242 A | * 10/1997 | Phan et al. | 606/198 |
| 5,944,701 A | 8/1999 | Dubrul | 604/264 |
| 6,059,815 A | * 5/2000 | Lee et al. | 606/209 |

FOREIGN PATENT DOCUMENTS

| | | |
|---|---|---|
| JP | 3023379 | 1/1991 |
| JP | 3059142 | 3/1991 |
| JP | 7290571 | 11/1995 |
| JP | 8199080 | 8/1996 |
| JP | 9109320 | 4/1997 |
| JP | 9123330 | 5/1997 |

OTHER PUBLICATIONS

H. Tobushi et al, Journal of Intelligent Materials Systems and Structure, vol. 8, Aug. 1007, pp. 711–718.
G. Bourbon et al, SPIE–Int. Soc. Opt. Eng. 1998, pp. 147–158.
H. Tobushi et al, JSME International Journal, Series 1, vol. 35, No. 3, 1992.
P. Krulevitch, Journal of Microelectromechanical Systems, vol. 5, No. 4, Dec. 1996, pp. 270–282.

* cited by examiner

Primary Examiner—Nasser Ahmad
Assistant Examiner—Jane Rhee
(74) Attorney, Agent, or Firm—Eddie E. Scott; Alan H. Thompson

(57) ABSTRACT

Micro-electromechanical tools for minimally invasive techniques including microsurgery. These tools utilize composite shape memory alloy (SMA), shape memory polymer (SMP) and combinations of SMA and SMP to produce catheter distal tips, actuators, etc., which are bistable. Applications for these structures include: 1) a method for reversible fine positioning of a catheter tip, 2) a method for reversible fine positioning of tools or therapeutic catheters by a guide catheter, 3) a method for bending articulation through the body's vasculature, 4) methods for controlled stent delivery, deployment, and repositioning, and 5) catheters with variable modulus, with vibration mode, with inchworm capability, and with articulated tips. These actuators and catheter tips are bistable and are opportune for in vivo usage because the materials are biocompatible and convenient for intravascular use as well as other minimal by invasive techniques.

29 Claims, 12 Drawing Sheets

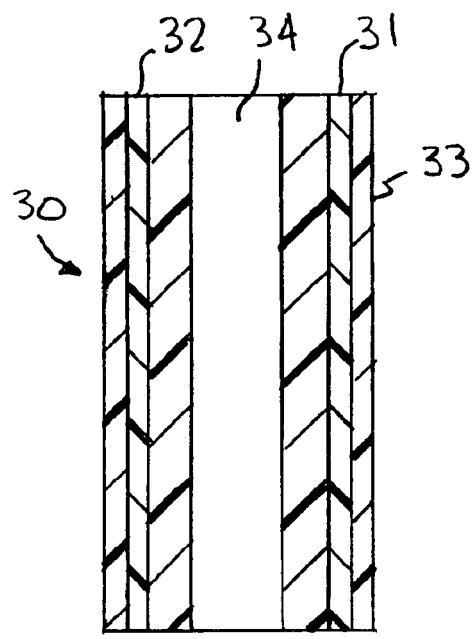
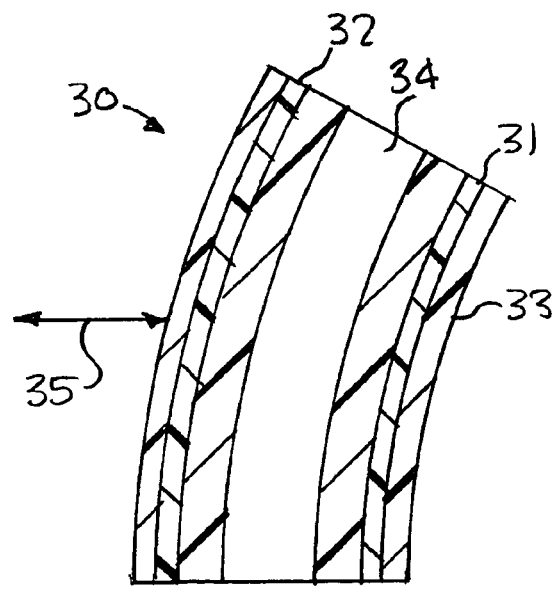
FIG. 7A   FIG. 7B
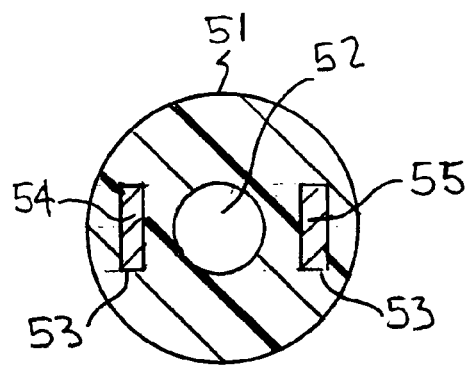
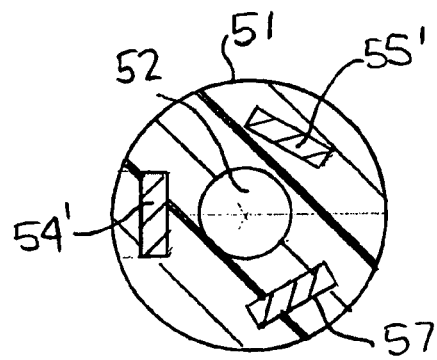
FIG. 10D   FIG. 10E

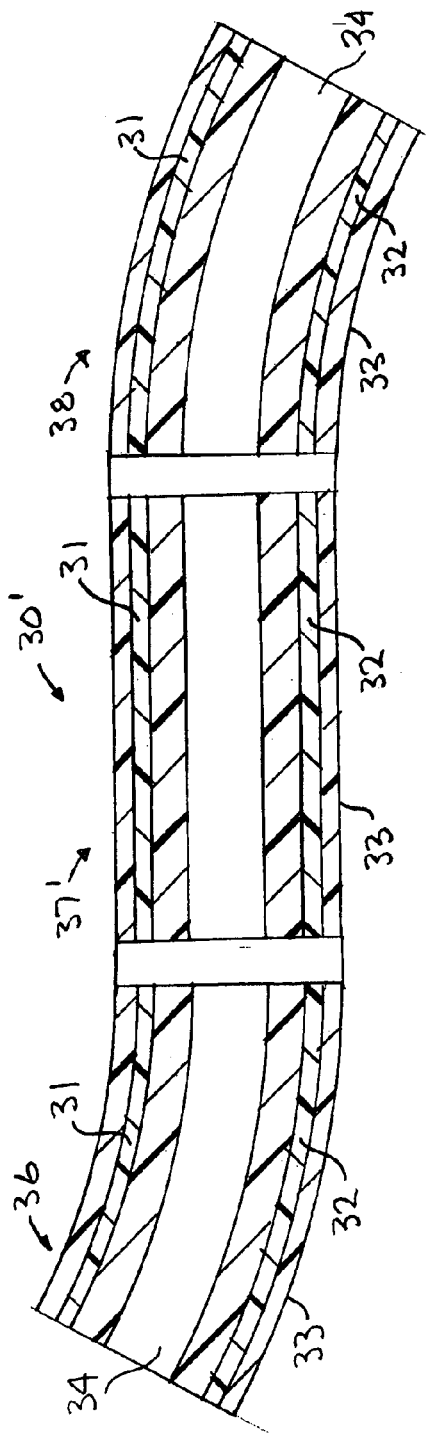
FIG. 8
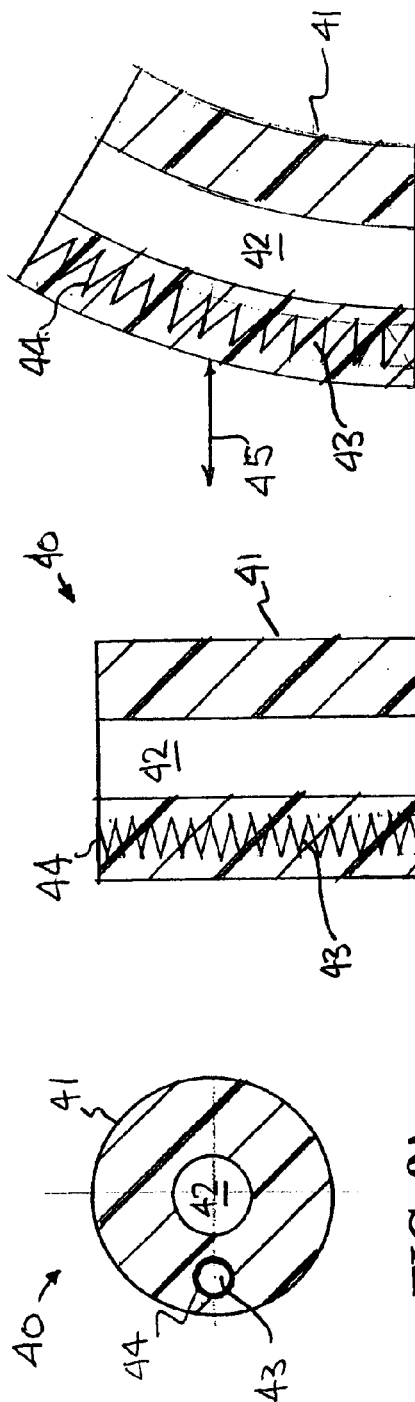
FIG. 9C
FIG. 9B
FIG. 9A

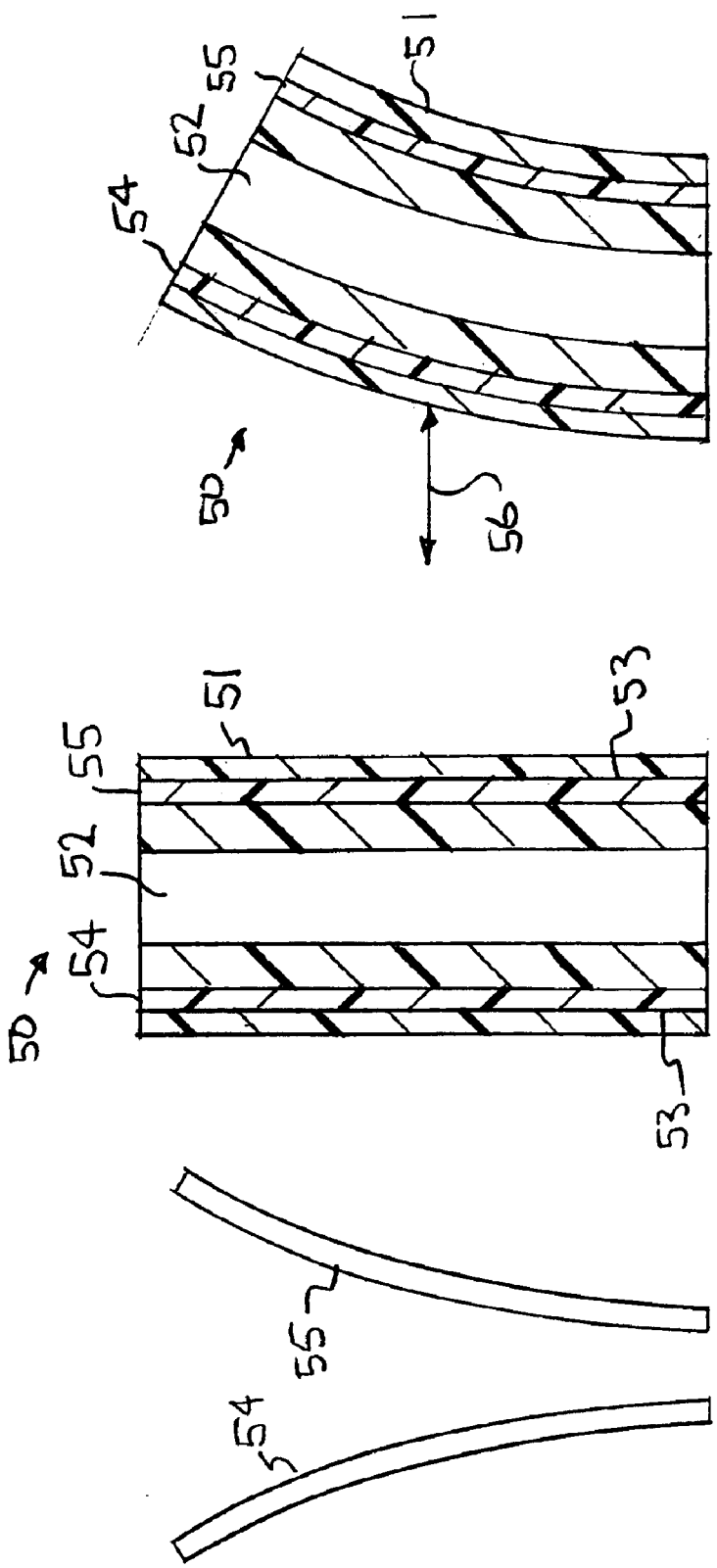

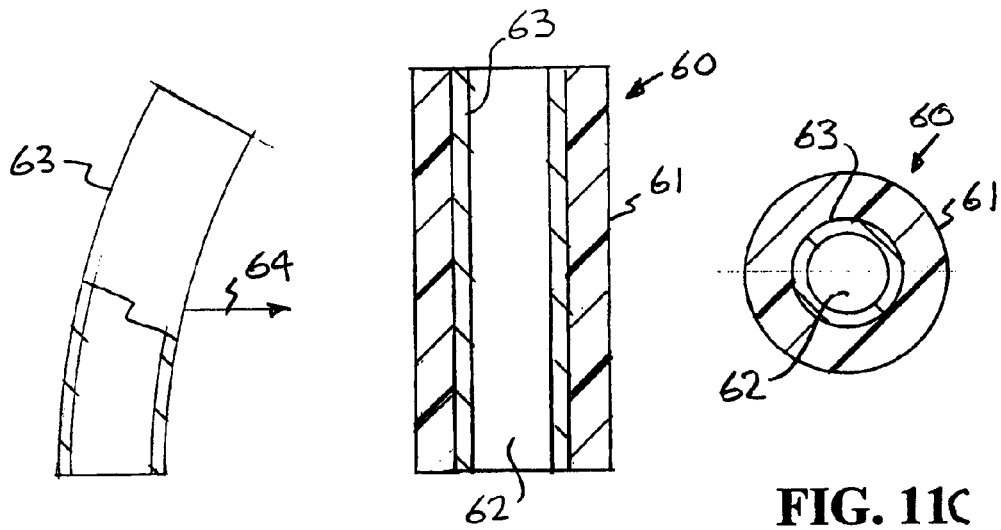
FIG. 11A   FIG. 11B   FIG. 11C
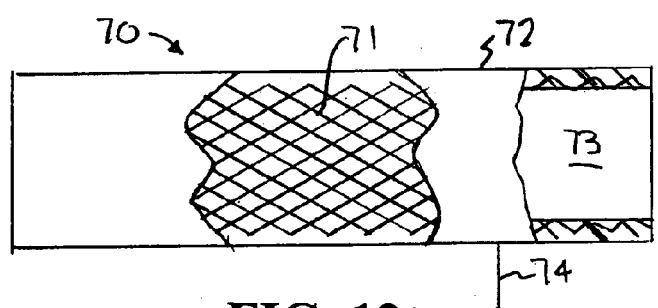 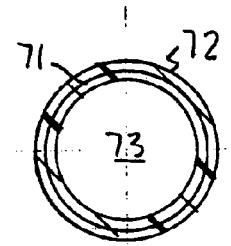
FIG. 12A   FIG. 12B
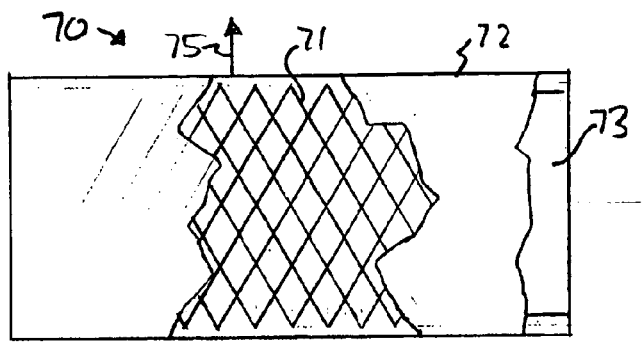 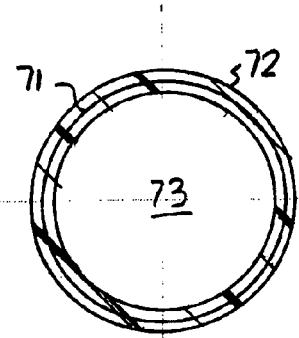
FIG. 12C   FIG. 12D

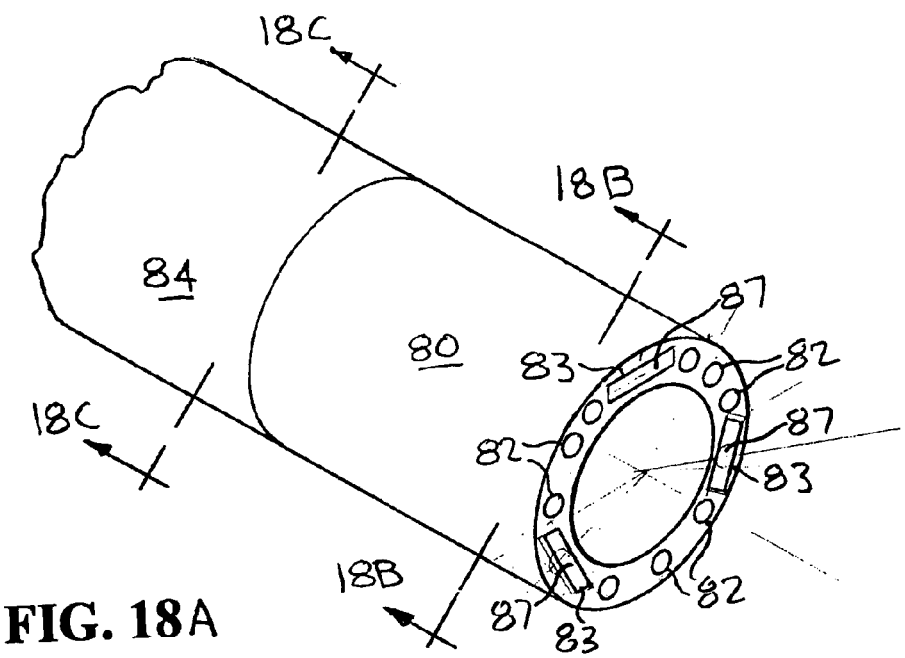
FIG. 18A
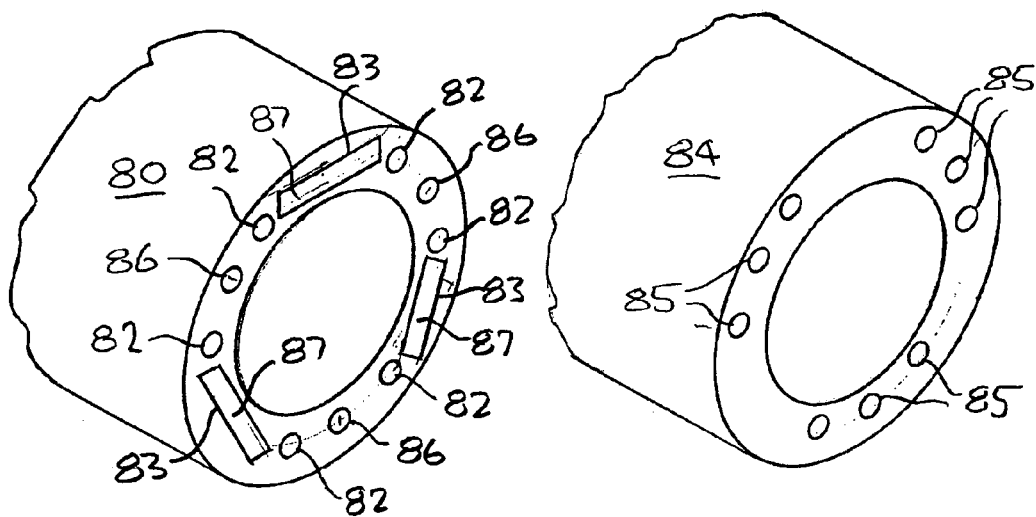
FIG. 18B FIG. 18C

SHAPE MEMORY ALLOY/SHAPE MEMORY POLYMER TOOLS

The United States Government has rights in this invention pursuant to Contract No. W7405-ENG-48 between the United States Department of Energy and the University of California for the operation of Lawrence Livermore National Laboratory.

BACKGROUND OF THE INVENTION

The present invention relates to tools for minimally invasive techniques, particularly to tools including catheter tips, actuators, etc. which use shape memory materials, and more particularly to minimal by invasive devices that have reversible translation and/or bending articulation capability to enable find positioning of tools, therapeutic device positioning, or therapeutic catheters by a guide catheter.

Biological and surgical micro electromechanical systems (MEMS), useful for their ability to be placed into and easily maneuvered around within the body, are being touted as the fastest growing area of micro-systems. For example, microcatheters are used in many medical applications for minimally invasive surgery. There are presently over 700,000 surgical uses of catheters per year in the United States, representing a market of many hundreds of million dollars.

As surgeons in the medical field continue to adopt and perform advanced surgical procedures, the miniaturization of medical devices is taking place and allowing surgery with small external incisions that grants access for these microsurgical tools by way of catheters. With roots in laparoscopic surgery (entering the abdomen through the navel and small holes in the midsection), minimally invasive surgery can currently be performed by inserting catheters in the femoral artery at the base of the thigh, navigating the blood vessels around the body, and arriving at problem areas like the heart or brain. Once the distal tip of the catheter is precisely placed inside the body, a microsurgical procedure like balloon angioplasty, stent placement, localized cauterization or drug delivery can take place. With the reduced bodily reaction to microsurgery and the minimization of scar tissue, these procedures are highly preferred over more typical "macro" surgery.

Surgeons who work with catheters have expressed a need for easier, more precise placement of the distal tip of the catheters. Upon rough placement of the tip (within ~2 cm), it would be advantageous to hold the proximal end of the catheter (toward the outside of the patient) 90% of the catheter in place, while articulating the distal end 10% with high accuracy and precision.

While catheter tubes have been created to fit through the vessels in the brain, these vessels are very tortuous and difficult to navigate with current techniques. The need exists for a method and means for articulating the distal tip to aid in maneuvering through the labyrinth of smaller diameter vessels like those in the neurovascular system.

Stents have been used in minimally invasive surgical techniques to open clogged arteries and veins to restore somewhat normal blood flow or to strengthen weakened vessels by adding a high modulus "patch" to the vessel wall. Stent problems needing a solution are reliable deployment (placing the stent correctly) and restenosis due to scalloping (an effect arising from the lack of a solid wall around the stent where materials can push through the stent's net-like weave and continue to occlude the vessel after the attempt at repair).

As pointed out above, the vasculature-especially the neurovasculature-is extremely tortuous forcing the catheter to follow several bends and turns before reaching its target destination. At times, abrupt turns into branching arteries are required. As a result, frictional effects between the catheter and vessel wall lead to a deterioration of the catheter tip maneuverability and control as more and more of the catheter is fed into the body. Static friction causes the catheter tip to bind, even when guide wires are used, which in turn causes the catheter to bunch up. Thus, there is a need for solutions to this problem, which are provided by the present invention and include a variable modulus catheter, a catheter with vibrational mode, an inch worm catheter, and a catheter with an articulating tip.

During the past decade, numerous approaches to solving the above-mentioned catheter related problems have been proposed, with many of the approaches involving the use of shape memory materials. Numerous papers, articles, and patents have been directed to these shape memory materials, as exemplified by H. Tobushi et al, "Thermomechanical Constitutive Modeling in Shape Memory Polymer of Polyurethane Series," Journal of Intelligent Material Systems and Structures, Vol. 8, pp. 711–718, August 1997; H. Tobushi et al, "Mechanical Properties of Shape Memory Polymer of Polyurethane Series (Basic Characteristics of Stress-Strain-Temperature Relationship)," JSME International Journal, series 1, Vol. 35, no. 3, pp. 296–302, 1992; G. Bourbon et al, "Three-dimensional active microcatheter combining shape memory alloy actuators and direct-drive tubular electrostatic micromotors," SPIE-Int. Soc. Opt. Eng., pp. 147–158, 1998; P. Krulevitch et al, "Thin Film Shape Memory Alloy Microactuators," Journal of Microeletromechanical Systems, Vol. 5, no. 4, pp. 270–282, December 1996; E. P. George et al, "Materials for Smart Systems Symposium," Maler, U.S. Patent Res. Soc. 1995, pp. 369–74; U.S. Pat. No. 5,405,337 issued Apr. 11, 1995, to R. S. Maynard; and U.S. Pat. No. 5,944,710 issued Aug. 31, 1999, to W. R. Dubual. Also see Japanese Patent Abstracts: JP 9109320A involving shape memory apparatus, for blow deflection flap driving mechanism etc, comprising shape memory composite member, Pettier device and heath radiator, providing high corrosion resistance and insulation properties; J1 81999080A involving shape memory composites, e.g. for endoscopes, temperature display, etc., comprising shape recovery temperature of shape memory alloy martenesile, and temperatures or generating power of alloy and polymer are identical; JP 7209571A involving high polymer molding product having reversible shape with temperature change prepared by making high polymer molding and shape memory alloy into composite product, etc.; JP 3059142A involving shape memory composite material-comprises woven filaments of shape-memory alloy, resin, etc., optionally in cylindrical form, optional of different shapes and shape-recovering temperatures; and JP 302-3379A involving shape-memory composite material used as spring, etc.-obtained by connecting shape memory parts of nickel-titanium alloy or polynorbomane-polystyrene-polybutadiene copolymer, with a connector.

The present invention provides solutions to the above-mentioned catheter related problems by the use of shape memory alloy (SMA), shape memory polymer (SMP) and combinations of these two shape memory materials which have bistable characteristics. The innovation of the present invention involves tools with reversibility capabilities fine positioning of the tools or distal end of the catheter, as well as reversible bending articulation of the distal tip, along with catheters having a variable modulus or vibrational mode and inch-worm capabilities as well as an articulated tip.

SUMMARY OF THE INVENTION

It is an object of the invention to provide tools to aid in microsurgery which include shape memory material.

A further object of the invention is to provide biological micro-electromechanical system tools which include shape memory materials in either singular or composite form.

A further object of the invention is to provide shape memory alloy/shape memory polymer composite, bistable actuators, which can be activated by means such as laser light via one or more optical fibers.

Another object of the invention is to provide a method and means for reversible fine positioning of a catheter.

Another object of the invention is to provide a method and means for reversible fine positioning of tools or therapeutic catheters by a guide catheter.

Another object of the invention is to provide a method and means for reversible bending articulation of the distal tip of a catheter to aid in navigation through the body's vasculature.

Another object of the invention is to provide methods using shape memory materials for controlled stent delivery, deployment, and repositioning.

Another object of the invention is to provide a catheter with means for maneuvering through the tortuous vasculature or neurovasculature by use of a catheter with: a variable modulus, a vibrational mode, and inch-worm arrangement, and an articulated tip.

Other objects and advantages of the present invention will become apparent from the following description and accompanying drawings. Basically, the invention involves methods and means (tools) for use with minimally invasive techniques. While these tools of the invention are particularly applicable for micro-surgical applications, they have non-medical applications such as nuclear stockpile monitoring with minimally invasive techniques. The description of the invention will be set forth relative to medical applications. By the use of shape memory alloy and/or shape memory polymer materials each of these materials and combinations being known in the prior, when utilized singularly, in combination, or as a composite tool have been developed which overcome the above-mentioned catheter use problems and which can be powered by heating via optical fibers. By using a combination or composite of a shape memory alloy (SMA) and a shape memory polymer (SMP), bistable tools for minimally invasive techniques are provided with reversibility capabilities which are particularly applicable for procedures involving delivery, deployment, and repositioning of devices such as stents in the vasculature or neurovasculature, as well as being provided with maneuverability of catheter tips. Actuators and catheter distal tips using shape memory material are opportune for in vivo usage because these materials are biocompatible and convenient for intravascular use because of their enormous work output to volume ratio as compared to competing microactuators. The combination of SMA and SMP material enables reversible fine positioning of a catheter tip, reversible fine positioning of tools, etc., reversible bending articulation of the distal tip of the catheter to aid in navigation through the body's vasculature. Use of one or both of the SMA and SMP materials allows a catheter tip to be produced with:

1) a controllable variable modulus wherein portions can be made stiff while other portions are selectively made complaint to enhance maneuverability, 2) a vibrational made formed to vibrate in regions where bending occurs, so that static friction is overcome, allowing eased advancement, 3) an inch-worm construction to induce a peristaltic, rippling effect to overcome static friction, or for self propulsion, and 4) an articulated tip producing a steerable catheter for greatly reducing static friction and potential snags in vulnerable regions.

BRIEF DESCRIPTION OF THE DRAWINGS

The accompanying drawings, which are incorporated into and form a part of the disclosure, illustrate embodiments of the invention and, together with the description, serve to explain the principles of the invention.

FIGS. 7A–7B illustrate an embodiment of a composite structure utilizing embedded SMA film ligaments forming a catheter tip or actuator for bending articulation.

FIG. 8 illustrates a device with a series of the actuators of FIG. 7A.

FIGS. 9A–9C illustrate an embodiment of a composite structure for bending articulation using an SMA spring embedded in one side of an SMP tube.

FIGS. 10A–10E illustrate an embodiment of a composite structure for bending articulation using a pair or more of curved SMA sections inserted into openings in an SMP tube.

FIGS. 11A–11C illustrate an embodiment of a composite structure for bending articulation using a bent SMA tube positioned in a hollow SMP tube.

FIGS. 12A–12D illustrate an embodiment of an SMA stent with a SMP wall coating for reversible deployment and positioning.

FIGS. 18A–18C illustrate an embodiment of a catheter articulating tip with symmetric SMA strips, power transmission fibers and laser diffusers located in a polymer tube, enlarged with FIGS. 18B and 18C taken along the lines 18B—18B and 18C—18C of FIG. 18A.

DETAILED DESCRIPTION OF THE INVENTION

Figure 1:
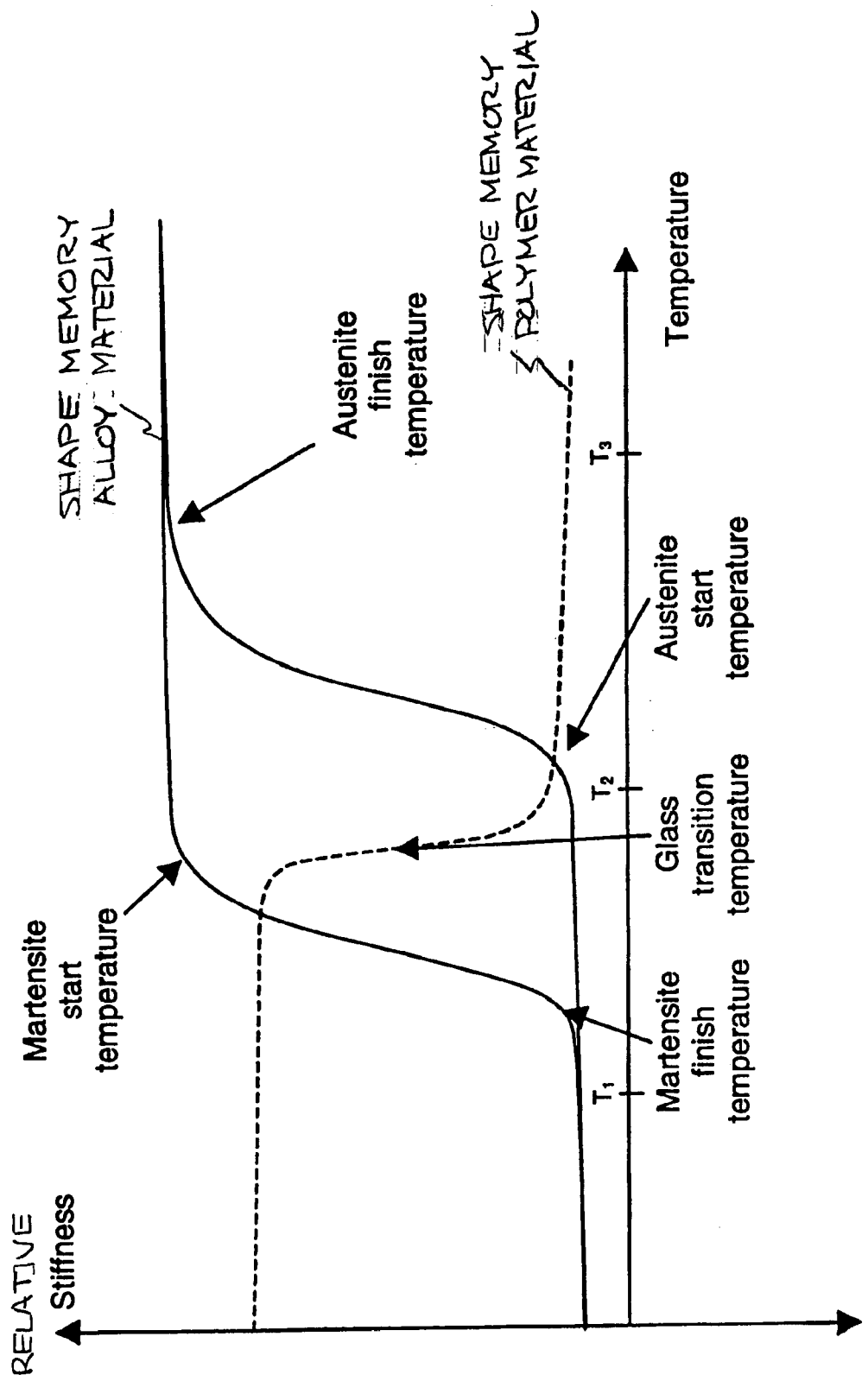
FIG. 1 graphically illustrates relative stiffness (elastic modulus) of SMA and SMP materials.
Figure 2:
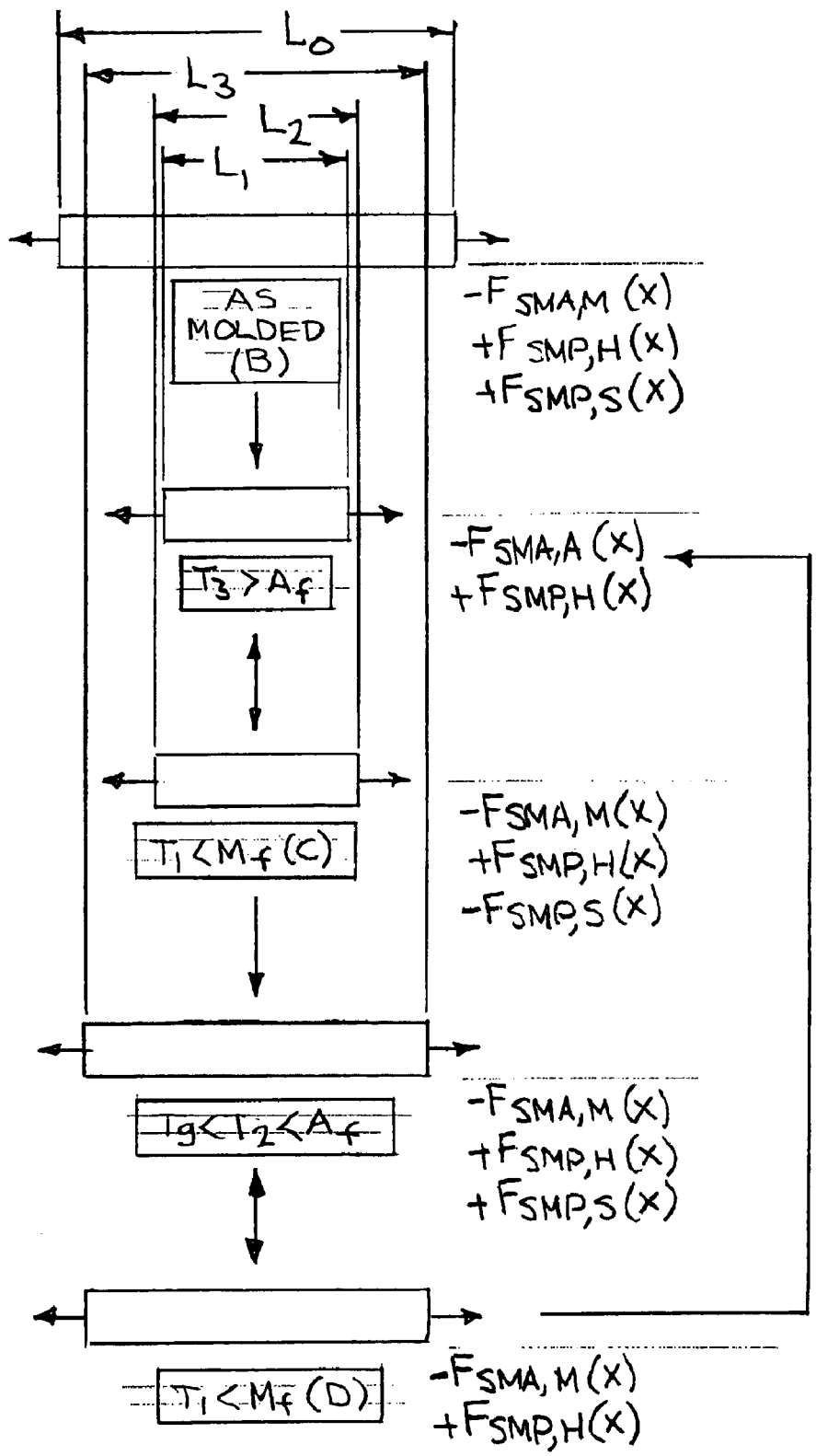
FIG. 2 illustrates the actuation cycle of the SMA/SMP composite tube structure.

The present invention is directed to methods and means (devices) which enhance the use of catheters for minimally invasive techniques, and which involve the use of shape memory alloy (SMA) and shape memory polymer (SMP) materials which can be used singularly, in combination, or as a composite. By the use of the shape memory materials, catheter tips can be made maneuverable, for example, and tools can be provided with reversible capabilities.

The invention involves a method using a combination or composite of SMA and SMP materials for: 1) reversible fine positioning of a catheter tip, 2) reversible fine positioning of tools or therapeutic catheters by a guide catheter, reversible bending articulation of the distal tip of the catheter to aid in navigation through the body's vasculature, and enabling controlled object (e.g. stent) delivery, deployment, and repositioning. In addition the invention involves methods for imbedding active elements (such as shape memory film or polymer) in the walls of the catheter, which may be powered, for example by heating via optical fibers, which enable maneuverability through the vasculature and the neurovasculature, whereby the frictional effects between the catheter and the vessel walls is diminished, thus eliminating or reducing deterioration of the catheter tip, as well as providing maneuverability and control of the catheter tip as the catheter is fed further into the body. By this invention catheters can be provided with: 1) a variable modulus (some portions stiffer than other portions), 2) a vibrational mode (made to vibrate in regions where binding) to allow for eased advancement, 3) an inchworm section (sidewall segments heated in succession) to induce a peristaltic, rippling effect, and produce self-propulsion, and 4) an articulated tip (embedded with shape memory materials) to provide steerability and reduce static friction and potential snags in vulnerable regions. The SMA/SMP composite actuator is bistable because the SMP can freeze the orientation while the SMA is in either of its two solid state phases.

The composite and combined structures of the invention incorporate both SMA and SMP materials wherein, for example, the SMA material is embedded within the SMP material as a bistable composite, or the SMA material is wrapped around the SMP material, or the SMA material is patterned on the surface of the SMP so as to enable reversibility.

Structures of the invention using either or both SMA and SMP materials involve employment of the shape memory material in the walls of a catheter.

Composite structures or actuators, made from preloaded shape memory alloy (SMA) springs, wires, or films and molded shape memory polymer (SMP), are created in different configurations to provide bistable actuation. Each actuator relies on the shape memory effects of the alloy and the polymer. The shape memory effect in an alloy occurs by a solid-state phase transformation during heating from a ductile martensite phase to a stiff austenite phase. During this phase transformation, strain deformations of up to 8–10% that had occurred in the lower temperature phase are recovered as the alloy "remembers" its shape. When the alloy cools, it transforms back to martensite at a lower temperature than it had transformed upon heating, thus experiencing hysteretic behavior.

The shape memory effect in polymer occurs by a phase transformation around the glass transition temperature of the polymer, outlined as follows:

The SMP is molded into an "original" shape.

Heating above the glass transition temperature causes a phase transformation, softening the polymer by two orders of magnitude. It is easily deformed in this state.

After deforming the polymer under loads, cooling below the glass transition temperature freezes it into the deformed state.

Heating in the presence of insufficient loads returns the polymer toward the "original" shape; subsequent cooling freezes it.

The transition temperatures of the alloy and the polymer can be designed into the materials with some degree of precision. The creation of a bistable composite actuator is accomplished by placing the glass transition temperature within the hysteresis of the alloy's transformation, as shown in FIG. 1 which shows the relative stiffness (elastic modulus) of SMA and SMP, and described hereinafter.

A composite structure is created by molding the polymer around the deformed alloy, as seen in FIGS. 3A–3D and FIG. 2. When this structure is heated above the austenite finish temperature of the alloy (also above the glass transition temperature of the polymer), the polymer becomes very soft and the alloy recovers a portion of its strain (see FIG. 3B). As the composite is cooled, the glass transition temperature is passed again before the alloy becomes ductile, so the structure's shape is frozen by the polymer. When the martensite finish temperature is reached, the cycle of heating is complete and the structure has changed shape. To reverse this shape change, the composite is heated above the glass transition temperature but below the austenite temperature of the alloy. The alloy remains ductile and deforms as the polymer recovers its shape. The structure is then cooled below the glass transition temperature to fix the shape. The two fixable shapes of this composite structure allow the bistable actuation illustrated in FIGS. 3C and 3D.

The SMA/SMP composite actuator is bistable because the SMP can freeze the orientation while the SMA is in either of its two solid-state phases. Shape memory alloys undergo a hysteretic solid-state phase transformation from martensite to austenite upon heating and back to martensite upon cooling. The hyteresis and applicable transformation temperatures are displayed in FIG. 1. When the alloy is annealed at high temperature, a highly organized body-centered, cubic lattice crystal structure is formed, causing a high stiffness in the alloy and the tendency to return to the organized shape. The shape at the annealing is thus called the memorized shape. When the alloy cools, it passes through martensite start ($M_s$) and martensite finish ($M_f$) temperatures as it transforms to the very ductile less organized martensite state. When the alloy is in this state, it easily holds deformation because the microstructure is allowed to reorganize to accommodate the deformation. This is not permanent plastic deformation however. Upon heating again, the alloy passes through it austenite start ($A_s$) and austenite finish ($A_f$) temperatures and transforms back to the highly organized lattice structure, recovering up to ~10% strains that were encountered in the martensite phase. The relative stiffness (elastic modulus) of SMA and SMP is seen in FIG. 1, with the placement of transition temperatures ($M_s$, $M_f$ and $A_s$, $A_f$) to create a composite actuator also displayed.

Shape memory polymer is mainly composed of cross-linked polymer chains of two types: soft segments and hard segments. Its molded shape is also its memorized shape, aside from some shrinkage upon curing. Rather than a hysteretic behavior, SMP has only one transformation temperature in the active temperature range of the composite known as the glass transition temperature $T_g$. At this temperature, the soft segments of the polymer melt and the elastic modulus decreases by more than 2 orders of magnitude. The polymer is very easily deformable above this temperature and if the deformation is held while the polymer is cooled, the now frozen soft segments hold the polymer's new shape. Upon heating again, the elasticity of the hard segments will return the polymer to its original shape (minus some possible plastic deformation) against loads according to Hooke's Law (Force=$k_{eff}$*displacement) in which $k_{eff}$ is the effective spring constant of the soft material.

To design a bistable actuator, the $T_g$ of the ploymer is strategically placed between the martensite start and the austenite start temperatures of the alloy. Shape memory alloy actuation is achieved by heating above the austenite finish temperature, at which point the polymer is very soft and the alloy can more freely return to its annealed shape with the recovered force of its shape memory effect. The polymer freezes before the alloy become ductile since $T_g$ is above Ms and the composite remains the state shown in FIG. 3D. Shape memory polymer actuation occurs when the opposite structure is heated to just above $T_g$ allowing the polymer to transform while the alloy is still ductile. The polymer's hard segments pull against the soft alloy spring and contract the composite tube structure freezing into FIG. 3C state upon cooling.

Because of the extreme modulus difference between shape memory alloy and shape memory polymer, as a rule of thumb, the SMP component must make up for the two order of magnitude lack in inherent material stiffness. Equilibration of the SMP component stiffness to the SMA component stiffness in composite devices can be achieved by one of the following three methods:

(1) Pure Scaling of Cross-Sectional Areas:

When a material is being purely stretched in tension, its stiffness is directly proportional to its cross-sectional area. Thus, if the SMA component has roughly 100 times less cross-sectional area than the SMP component and both are stretched in tension, the stiffness of the two components nears equilibrium. The design of actuators that utilize this equilibration method must account for possible buckling modes of either component. Usually, buckling of an element will cause an unstable actuation from which recovery is impossible. See FIGS. 7, 14&16.

(2) SMA Bending vs. SMP Tension

Another way to lower the stiffness of the SMA relative to that of the SMP is to put the SMA into a bending mode while keeping the SMP in a tensile mode. An example of this equilibration method is a coiled SMA spring acting against a tensile SMP component. This is best seen in FIGS. 3A–3D, 9A–9C, 10A–10E, 11A–11C, 12A–12D, and 13 A&B.

(3) Material Location with Respect to a Central Axis (Central Axis Theorem)

If both SMA and SMP are incorporated into a bending actuator, the stiffness that a material contributes to the overall stiffness of the actuator is governed by its relative distance from the central axis of the part. As material is moved away from this central (or centroid) axis, the stiffness of the part is increased as the square of the distance from the central axis. The reason behind this: the farther material is from the central axis, the more it is under tension rather than bending.

During experimental verification of the SMA/SMP composite, it has been determined that to produce a bistable actuator, the SMA member (coil or spring) should be stretched and annealed, then compressed and embedded within the SMP material (tube or cylinder) rather than starting with a SMA member annealed to its unstretched length, then stretched and embedded within the SMP material, which results in unstable buckling modes. FIGS. 3A–3D illustrate an SMA spring embedded in circumference of an SMP tube to cause lengthwise extension and radial contraction.

Figure 3D:
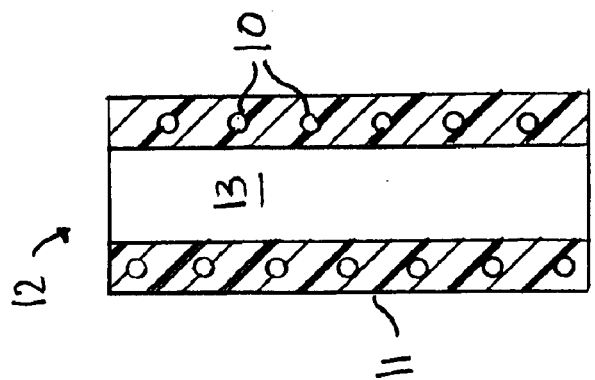
FIGS. 3A–3D illustrate the construction of a composite, bistable SMA/SMP device, and the associate length and diameter changes under different temperature conditions.
Figure 3C:
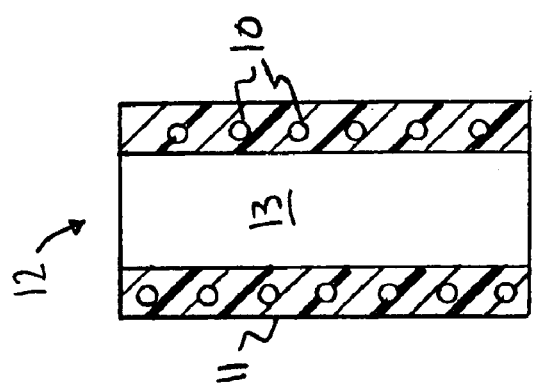
Figure 3B:
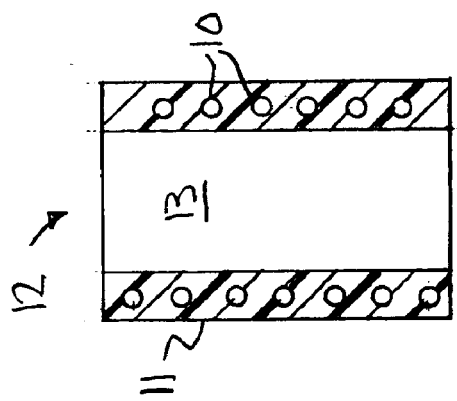
Figure 3A:
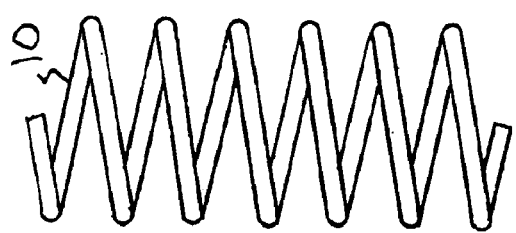

The composite of FIGS. 3A–3D shows in FIG. 3A an extended or stretched SMA spring 10, in FIG. 3B, the SMA spring 10 is compressed or deformed with an SMP tube 11 molded around it and cooled to ambient temperature to produce a structure 12 with an opening 13; in FIG. 3C, the composite structure 12 is shown after the SMP tube 11 cures allowing the structure 12 to come to an equilibrium. When both the SMA spring 10 and the SMP tube 11 are heated above their transformation temperatures, the SMA spring 11 extends the structure 12 causing a radial contraction and stretching the SMP tube 11 as seen in FIG. 3D. When the structure 12 is then heated above the SMP transition temperature but below the SMA transformation temperature, the SMP tube 11 will pull back toward its as-molded shape and compress the ductile SMA spring 10 and reverse to that of FIG. 3C.

As seen in FIGS. 3A–3D, spring 10 in FIGS. 3A–3D has a diameter ($d_A$) and length ($L_A$), diameter ($d_B$) and length ($L_B$), diameter ($d_C$) and length ($L_C$), and diameter ($d_D$) and length ($L_D$), wherein diameters: $d_B > d_c > d_D > d_A$, and wherein lengths $L_A > L_D > L_c > L_B$. Also, as the diameter of the SMA spring 10 changes, the diameter of the SMP tube 11 changes and thus the diameter of the opening 13 in SMP tube 11 changes, whereby a device or object can be retained by or released from the structure 12, which may constitute an actuator for delivery of medicines, etc.

The first applications of this composite structure are for the positioning of a catheter tip. These configurations most resemble the tube in FIG. 3C. A shape memory alloy spring is annealed to a certain length and diameter. When deformed by stretching, the diameter of the spring shrinks, and when deformed by compression, the diameter expands. The spring is deformed in its ductile phase and SMP is molded around it, forming a tube of roughly the same diameter of the spring. As this structure is heated and cooled, the length and diameter of the tube change. When three or more of these are placed in series, see FIGS. 4 and 5, an inchworm type actuator is created in which the first or last actuator in the series can have an expansion in diameter to hold the tube against the arterial wall while the central actuators expand in length to position the catheter tip. Similarly, a tube can be created in which the tube walls contract to grab and manipulate structures within the tube as shown in FIG. 5. This is useful as a guide catheter to precisely manipulate therapeutic catheters inside the body. The two possible useful configurations with this actuator are therefore 1) diameter expansion/contraction upon actuation, and 2) length expansion/contraction upon actuation.

Figure 4:
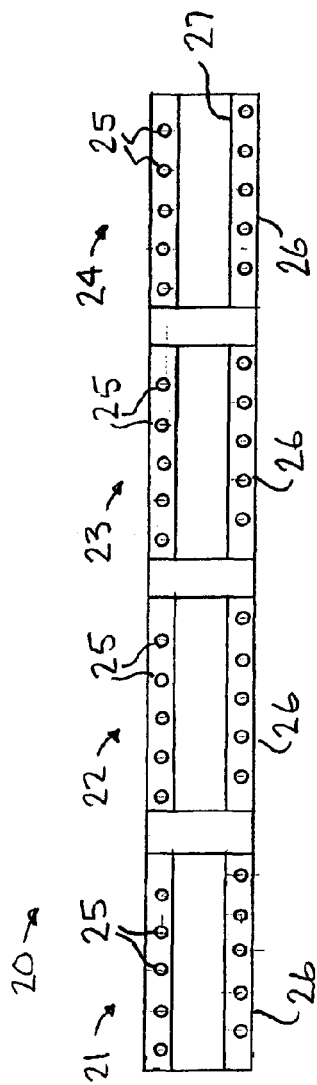
FIGS. 4–6 illustrate different embodiments of a multi-unit actuator using composites as in FIGS. 3A–3B wherein the length or diameter is changed by heating various units connected in series.
Figure 5:
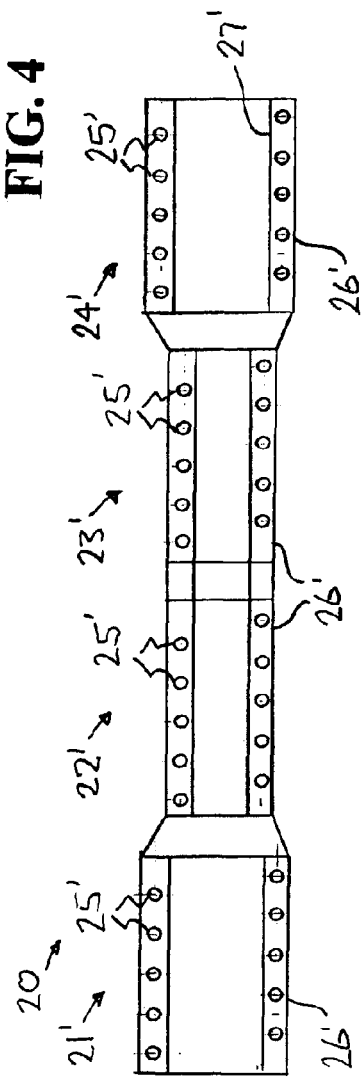
Figure 6:
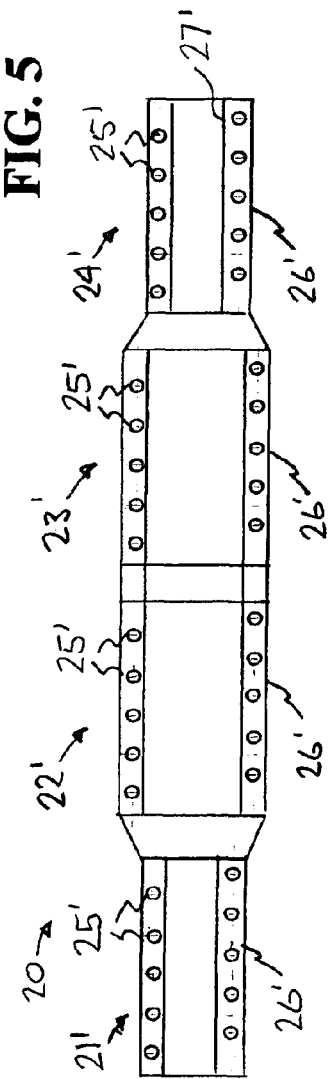

As shown in FIG. 4 the actuator, generally indicated at 20, comprises four composite SMA/SMP units 21, 22, 23 and 24, constructed as described wherein the units 21–24 comprise an SMA coil 25 molded in an SMP tube 26, having a longitudinally extending opening 27. As shown in FIG. 5 end units $21^1$ and $24^1$ are of a larger diameter exterior and internal opening $27^1$ than central units $22^1$ and $23^1$, while in FIG. 6 the central units $22^1$ and $23^1$ are for a larger diameter exterior and central opening $27^1$ than end units $21^1$ and $24^1$. The difference in the configurations of FIGS. 5 and 6 being caused by selected heating of the SMA coils 25 and SMP tubes 26. The heating may be carried out by fiber optics, known in the art, connected to a controlled light source, such as a laser.

The next embodiment of the composite structure is for bending articulation of a catheter tip. This catheter is created by imbedding multiple SMA coils or springs or SMA strips or films radically within the tube wall such that the spring or film diameter is slightly smaller than the wall thickness of the tube. When individual springs or films are heated in a configuration, like this one, that part of the tube expands or contracts in the tube wall causes bending of the entire tube and translates into multi-directional articulation at the catheter tip. Embodiment of the composite bending structure is depending on the preloading conditions of each spring or film. This localized expansion illustrated in FIGS. 7A–7B, 8, 9A–9C, 10A–10E, and 11A–11C, wherein each of these actuation mechanisms hinges on the difference of the transformation temperatures of the SMA and the SMP and the equilibration of stiffness by the rules of thumb outlined above.

The embodiment of FIGS. 7A–7B and 8 involves embedding SMA films on the order of 1 micron thick within an SMP matrix on the order of 0.1 mm thick. Heating the SMA film ligaments on one side of the device induces bending in one direction due to a residual tension stress in the SMA film. As the SMA film is heated the temperature of the SMP matrix also rises above its transition, bringing the SMP into its highly deformable rubbery state. Film ligaments on the opposite side of the device are heated to cause bending in the other direction. Heating may be carried out, for example, via optical fibers or by resistive heating of the film ligaments.

As seen in FIGS. 7A and 7B, a device or actuator 30 includes SMA film ligaments 31 and 32 embedded in a hollow SMP tube 33 having an opening 34. When SMA film ligament 31 is heated the ligament is caused to contract causing a bending of the device 30 as seen in FIG. 7B. Heating of the SMA film ligament 32 would cause the device 30 to bend in an opposite direction whereby the device 30 is of a double-action type as indicated by arrow 35.

FIG. 8 illustrates a series of devices as in FIGS. 7A–7B, and corresponding components are given corresponding reference numbers. As shown, a device or actuator $30^1$ is provided with three units 36, 37 and 38, each constructed as in FIG. 7A. By heating the SMA film ligament 31 of unit 36 the unit bends in one direction that of unit 36. To provide additional bending action, either of the SMA film ligaments 31 or 32 of unit 37 can be heated. Again, the device 30 of FIGS. 7A–7B and each of the units 36–38 of FIG. 8 may be heated, for example, by controlled light energy or by resistive heating, each approach being known in the art.

Another approach for bending articulation is to use the SMP in tension and the SMA in the more compliant bending mode, such as the coiled spring configuration. If the SMA spring is placed off-axis in an SMA/SMP composite, it will induce bending in the device, as shown in FIGS. 9A–9C, with FIG. 9A being an end view of FIG. 9B. As shown, the structure (actuator or tip) 40 comprises a hollow SMP tube 41 having a central opening 42 and an off-axis opening 43 within which a compressed SMA spring 44 is located covered at each end with SMP. Heating of the structure 40 above the SMA transformation causes off-axis extension as indicated by arrow 45, and as shown in FIG. 9C. The compressed SMA spring 44 may be molded within the SMP tube 41.

The embodiments of FIGS. 10A–10E rely on bending differences and the Central Axis Theorem, discussed above, to equalize the stiffness of pre-bent SMA members or sections inserted into openings in the wall of the SMP tube. When these SMA members are heated individually and the SMP is heated above its transition temperature, the SMP tube bends preferentially toward the actuated SMA member. The antagonistic components can then pull the tube back to its straight orientation. In this embodiment, the SMA and SMP are not rigidly fixed together because that would place the SMA members in tension rather than bending, which is not useful.

As shown in FIGS. 10A–10E an actuator or structure generally indicated at 50 is composed of a hollow SMP tube having a central opening 52 and a plurality of off-axis openings 53 into which bent SMA sections or members 54 and 55 are inserted, with FIG. 10A illustrating the original shape of SMA sections 54 and 55. Selectively heating SMA section or member 55 causes that section to curl back toward its original shape, causing bending of the structure 50 as indicated by arrow 56, and as shown in FIG. 10C. As shown in cross-section in FIGS. 10D and 10E, two or three spaced SMA sections or members, or more, may be utilized with FIG. 10E adding an additional SMA section or member 57, with SMA sections $54^1$, $55^1$ and 57 equally spaced about central opening 52 in SMP tube 51.

The embodiment of FIGS. 11A–11C relies purely on the Central Axis Theorem to add stiffness to the SMP relative to the SMA and cause a uni-directional bending mode. The embodiment is shown in a hollow tube configuration, but can also be used in a bending bimorph cantilever configuration when an open catheter lumen is required. The illustrated embodiment involves a bent SMA tube embedded into an SMP tube. As shown, the structure or actuator 60 comprises an SMP tube 61 having a central opening 62, as shown in FIG. 11B, into which is embedded a bent SMA tube 63 as indicated by arrow 64, and as shown in FIG. 11A, and which results in the SMA tube 63 being straightened as shown in FIG. 11B. Upon heating the structure 60, the SMA tube 63 bends toward its original shape causing the structure 60 to bend, allowing a one direction of bending action.

The final configurations for a composite stent made from SMA and SMP are shown in FIGS. 12A–12D and 13A–13B. Currently, some stents are made from a super elastic SMA that has transition temperatures lower than the ambient temperature and therefore resides in its austenite phase. When high enough forces are placed on this material, the martensite phase transformation occurs with no temperature change, resulting in ductile material. When the load is removed, the austenite transformation brings the material back to its rigid state. A stent is created from this material by weaving a net-like tube that experiences high changes in diameter with changes in length. A stent is inserted by collapsing the diameter (extending the length), inserting into the artery, and releasing the load when the stent is in place so that it presses against the artery wall. The invention is to control this stent release by coating the stent with SMP, forming a tube structure. Three configurations exist here. 1) If the stent is collapsed before the SMP is molded around it, heating above the glass transition temperature allows the stent to expand against for force of the polymer. This is a slow controlled release. 2) If the SMP is molded around the uncrushed stent, then heated above the glass transition temperature while collapsing the stent and cooling to freeze into place, actuation by raising the temperature expands the stent with aid from the polymer. This is a quicker, more forceful release. 3) The stent could be made from martensitic rather than superelastic SMA. By setting the shape of the SMA stent as a narrow tube but molding SMP around it when expanded (or vice versa), the two shape memory effects could act opposite each other to both open and close the stent during precision placement.

Reversible delivery, deployment, and repositioning of devices such as stents and embolic material can be achieved using an SMA/SMP actuator. The device can either be incorporated into the tip of a catheter, or form the stent itself. When used as a stent, a coiled element or net-like tube of SMA material is embedded into an SMP sheath. If a SMA spring is utilized, it is compressed during the SMP molding process, and expands when heated above the SMA transformation temperature, applying and outward pressure on the blood vessel. If improperly positioned, the device can be heated above the SMP transformation (but below the SMA transformation) temperature, at which point the SMP sheath will recompress the SMA spring, and the stent will shrink to its original diameter. When forming the tip of a catheter, the SMA/SMP actuator can be made to expand in diameter or length, and shrink in order to release, position, or grab therapeutic devices.

Figure 13A:
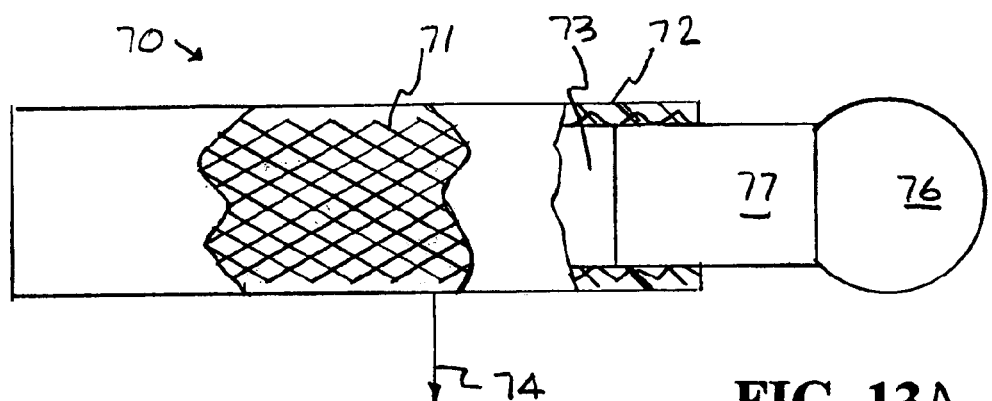
FIGS. 13A–13B illustrate an embodiment, similar to that of FIGS. 12A–12D, for release and recapture of a deliverable object.
Figure 13B:
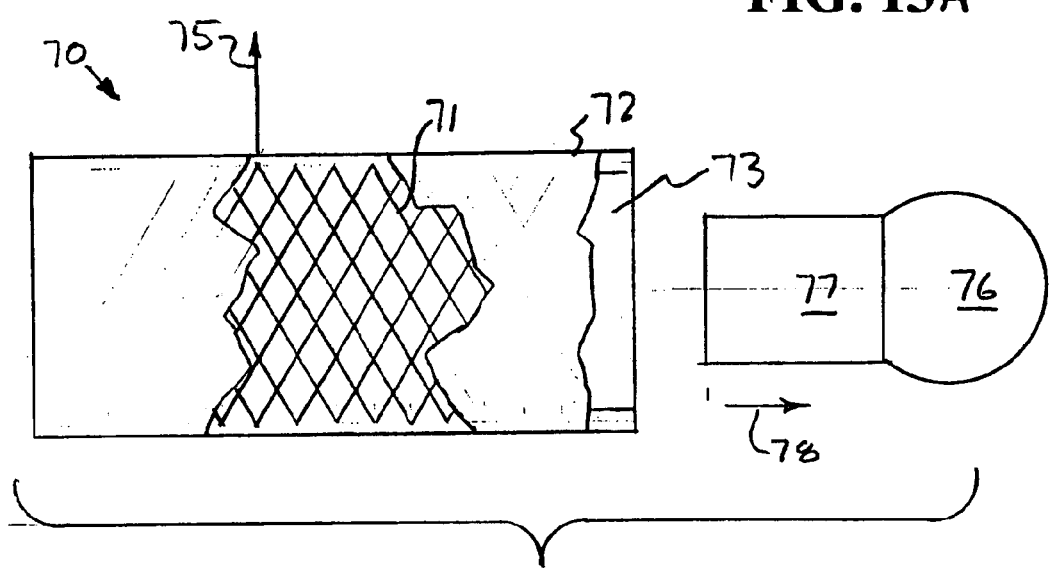

The embodiments of FIGS. 12A–12D and 13A–13B utilize a stent created from SMA material by weaving a net-like tube that is embedded in a SMP sheath or tube. The action of opening and closing of a stent is shown in FIGS. 12A–12D, while the action of releasing and recapturing a deliverable object is shown in FIGS. 13A–13B.

FIGS. 12A–12D illustrates a SMA stent with a SMP wall coating for reversible stent deployment and positioning. As shown, the actuator embodiment 70 comprises net-like SMA stent 71 with a SMP wall or coating 72, as shown in FIG. 12A, whereby the stent 71 is embedded within the SMP wall 72, having a central opening 73, as seen in FIG. 12B. Applying heat above SMA and SMP transformation temperatures causes the SMA stent 71 and SMP wall 72 to enlarge in diameter and shrink in length as shown in FIGS. 12C and 12D, and as indicated by arrow 74, whereby the stent 71 is opened, for use such as supporting a wall of a blood vessel. By then applying heat only above the SMP transformation temperature the stent 71 and SMP wall 72 shrink in diameter and stretch in length and thus return to the original configuration shown in FIGS. 12A–12B, as indicated by arrow 75, whereby the stent 71 can be repositioned or removed.

The embodiment of FIGS. 13A–13B is the same as that of FIGS. 12A–12D except that device functions to deliver and/or recapture an object, but may also function as a stent, as in FIGS. 12A–12D. Similar components to those of FIGS. 12A–12D have been given corresponding reference numerals in FIGS. 13A–13B. As shown in FIG. 13A an object 76 to be delivered is retained in opening 73 of the structure 70 via reduced diameter section 77. Upon deployment by a catheter, for example, to a desired location, the structure 70 is heated to change configurations shown in FIG. 13B and the object 76 is released as indicated by arrow 78 when the structure 70 changes configuration from that of FIG. 13A to that of FIG. 13B due to heating as described above. To recapture the object 76 the structure is positioned around reduced diameter section 77, as by a catheter, and heated, as described above, causing the structure 70 to again revert to its original shape, as indicated by arrow 75, as shown in FIG. 13A whereby the object 76 is again retained (recaptured) by the structure 70 and can be repositioned or removed as desired. After depositing the object 76, the structure 70 may be utilized as a stent, or again reduced in diameter and repositioned and expanded in diameter for use as a stent, for example.

The present inventions provides a catheter with the capability to navigate the tortuous neurovasculature without deterioration of the catheter tip due to frictional effects between the catheter and the vessel wall, and to enable control of the catheter tip as more and more of the catheter is fed into the body. This is accomplished by the use of shape memory materials, either as shape memory films embedded in the walls of the catheter, which may be composed of a shape memory polymer, or as a shape memory wire wrapped around a tube of shape memory polymer, or by constructing the catheter of different material to produce a variable modulus, or to embed piezoelectric materials in the walls of the catheter to produce vibration of the walls, or to construct segments of the catheter wall with shape memory alloy films to produce a catheter with inch-worm capabilities, as well as a catheter with an articulated tip. Thus, this invention enables the formation of: 1) a variable modulus catheter, 2) a catheter with vibrational mode, 3) an inch-worm catheter, and 4) a catheter with an articulated tip.

Figure 14:
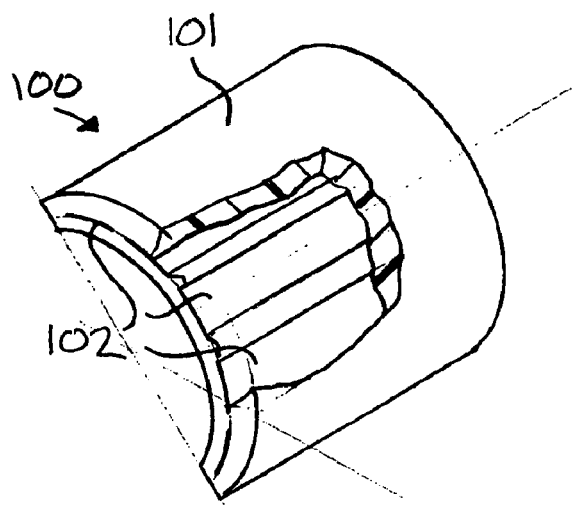
FIG. 14 is a partial cross-section of a catheter or actuator section composed of shape memory film/polymer composite, with the outer surface removed for clarity, made with microfabrication techniques, and provides selective axial displacements.
Figure 15:
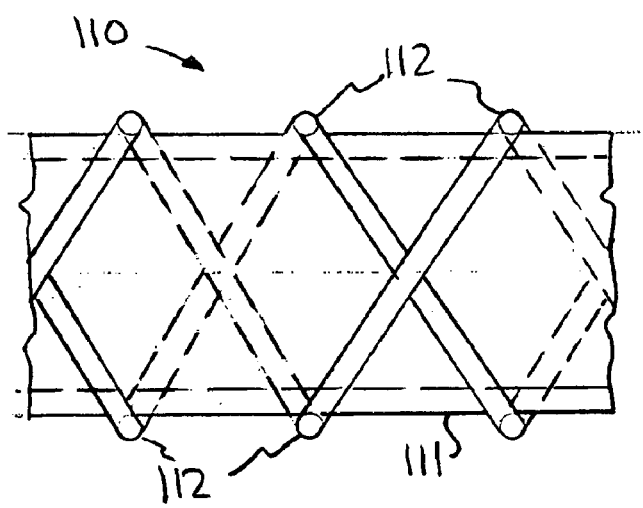
FIG. 15 illustrates a section of an actuator or catheter composed of shape memory polymer with a wire of ribbon of shape memory alloy wrapped therearound.

These four (4) approaches to catheter manuverability are carried out by forming one or more sections of the catheter wall, which may or may not be composed of SMP, with embedded SMA films or ribbons, as shown in FIG. 14, or by wrapping an SMA ribbon or wire around an SMP tube as shown in FIG. 15, described hereinafter. Each of the four catheter approaches using shape memory materials are separately described hereinafter.

Variable Modulus Catheter:

By producing a catheter with controllable variable modulus, portions can be made stiff while other portions are selectively made compliant to enhance maneuverability. Approaches include polymer-based catheters which have a temperature sensitive modulus, and catheters with shape memory film elements embedded in the wall. Energy could be selectively delivered to segments of the catheter curved beyond a critical radius using optical fibers which leak light when bent. Another approach is to inject cold saline solution into a catheter formed from a polymer having a temperature-controlled modulus. The catheter could be made entirely of a temperature-sensitive material, in which case a variable length of the catheter could be stiffened, depending on flow rate of the cold solution, starting at the proximal end of the catheter. Alternatively, the catheter could be constructed of different materials, such that only select regions would be transformed by the temperature change.

Catheter With Vibrational Mode:

If the catheter can be made to vibrate in regions where it is binding, static friction will be overcome, allowing for eased advancement of the catheter. Polymeric piezoelectric materials, and catheters with embedded piezoelectric materials including shape memory alloys may be used for this application. Opto-acoustic transduction is another potential solution to this problem, with the advantage of optically-delivered power.

Inch-Worm Catheter

Segments of shape memory alloy can be embedded into the catheter sidewall, which may be composed of shape memory polymer or other polymer, and the segments are heated in succession to induce a perislatic, rippling effect. This approach could be used to overcome function, or possibly even for self propulsion of the catheter tip. Another approach is to use three balloon-type elements at the catheter tip, which when inflated in succession, would advance the catheter tip using a (1) grab-(2)advance-(3)grab-(1) release in sequence. This device could be actuated either hydraulically or thermo-pneumatically.

Catheter with Articulated Tip

Producing a steerable catheter would greatly reduce static friction and potential snags in the most vulnerable region: the catheter tip. Embedded shape memory films or the incorporation of other active materials into the catheter wall is the key to producing such a device. The shape memory films can be activated via optical fibers, for example.

While the ultimate goal of the development program under which the present invention arose was to develop catheter tip articulation, the variable modulus catheter and vibrational mode catheter were developed, along with the inch-worm catheter.

During the development of the variable modulus catheter, two approaches were considered. The first used variable modulus polymers for one or more sections of the catheter. The material was selected so as to be compliant at body temperature, and stiffened by lowering the temperature by injecting cold saline solution. One drawback of this method is that the heating or cooling is done along the whole length of the catheter.

The second approach to achieve more localized modulus control, involved an active composite material consisting of thin film shape memory alloy (SMA) ribbons embedded in a polymer matrix (see FIG. 14). The Lawrence Livermore National Laboratory (LLNL) has developed a unique capability for sputter-depositing nickle-titanium-copper SMA films that are ideally suited to in vivo medical applications (see above referenced P. Krulevitch et al article). Unlike typical NiTi SMA alloys, the LLNL's NiTiCu films have thermo-mechanical properties that are insensitive to compositional variations. Moreover, these films begin their transformation just above body temperature and have a narrow hysteresis width (8 degrees compared to 40 degrees for NiTi), and therefore require minimal power input for actuation. Thorough mechanical characterization has proven these films to be highly ductile, and capable of sustaining stresses greater than 400 MPa and strains up to 8% with no observable plastic deformation after shape recovery.

Figure 16:
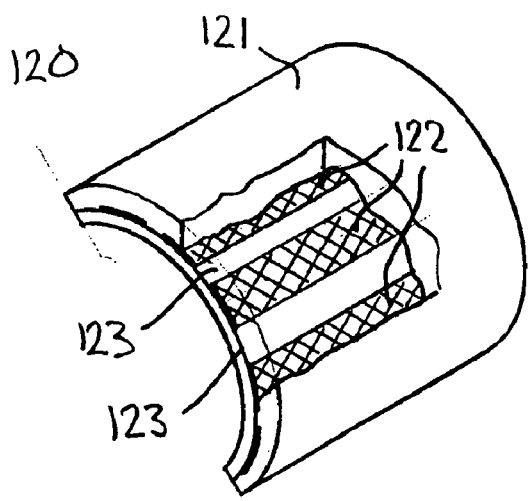
FIG. 16 illustrates an embodiment similar to FIG. 14 except the SMA film ribbons are composed of foil meshes formed by a process for releasing patterned sections of SMA film from the substrate.

Also during the development program under which the invention arose, consideration was given to a process for releasing patterned sections of SMA film from the substrate to form foil meshes. These foil meshes, attached to structural anchors, will be embedded in a polymer matrix, similar to that of FIG. 14, using an extruder. When at body temperature, the metal/polymer composite will be highly flexible, similar to conventional guide wires and catheters. Selectively heating sections near the catheter's tip will cause the affected SMA ligaments to contract and stiffen due to a combination of shape memory effects and the modulus change associated with the transformation. One potential mechanism for selectively heating the active sections is to dye the polymer to preferentially absorb laser energy of a particular frequency. Light will be delivered via an optical fiber internal to the smart catheter. Different frequencies and dye colors will be used to activate different sections of the catheter. FIG. 16 described hereinafter illustrates an embodiment incorporating foil meshes. The process for producing the foil meshes briefly involves sputter-coating shape memory alloy onto a flat substrate with a release layer between the film and the substrate and subsequently patterning the film into the desired mesh shape using standard photolithographic processes. This mesh pattern can be lifted off the substrate as a single entity by dissolving the sacrificial layer from beneath the shape memory alloy. Alternatively, a shape memory polymer or other polymer layer can be cast onto the shape memory alloy film and when the sacrificial layer is dissolved away, the shape memory alloy and shape memory polymer remain in contact and a composite structure is formed. Furthermore, after removing this composite film from the substrate, a second shape memory polymer or other polymer layer can be cast onto the opposite side of the shape memory alloy to fully encapsulate the alloy. The laminated structure can then be attached to a tube or formed into a tube on its own to create the embodiments described hereinafter.

A similar approach can be used to embed active piezoelectric elements, like PZT or ZincOxide into catheter walls to provide the catheter with a vibrational mode which can be made to vibrate in regions where there is binding due to static friction, as discussed above.

Figure 17:
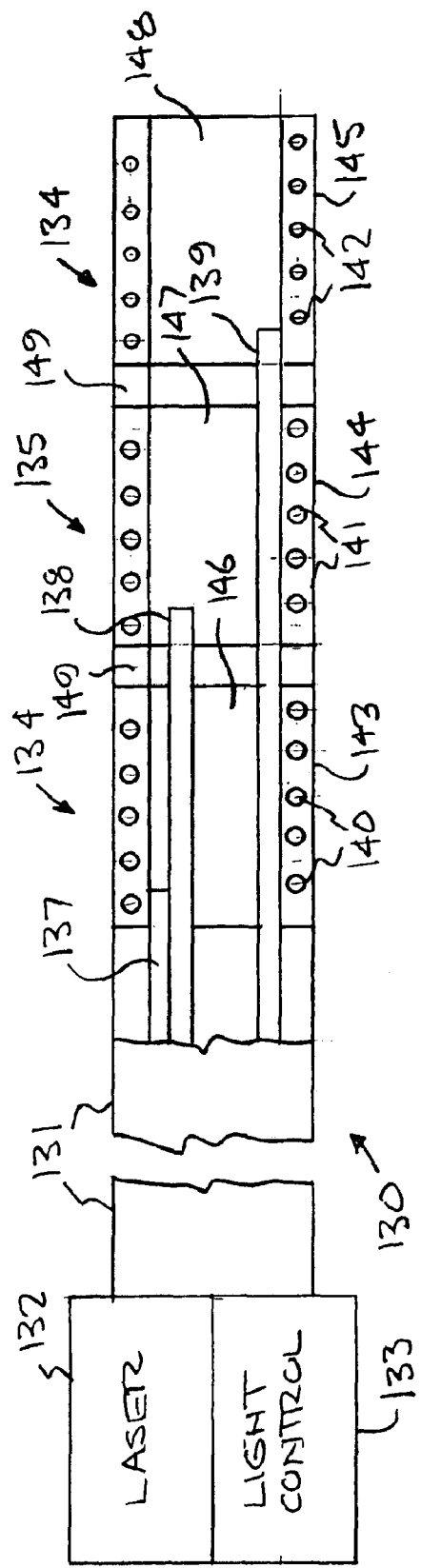
FIG. 17 illustrates an embodiment of an overall catheter system utilizing two composite SMP/SMA units of the present invention, with controlled laser light/optical fiber activation thereof.

In each of the approaches, the active materials may be heated by optical fibers which may transmit laser light, for example as illustrated in FIG. 17 described hereinafter. The actuators or catheter wall sections may be activated and controlled by a system such as described and claimed in copending U.S. application Ser. No. 09/713,988, filed Nov. 16, 2000, entitled "Medical Devices Utilizing Optical Fibers For Simultaneous Power, Communication and Control", and assigned to the same assignee.

Referencing now to FIGS. 14, 15 and 16, only a portion of an actuator or catheter wall is illustrated using embedded SMA material (FIG. 14), or wrapped SMA material (FIG. 15), or embedded SMA foil mesh (FIG. 16).

As shown in FIG. 14, a composite actuator or catheter section, generally indicated at 100 comprises a polymer sheath 101 the exterior surface being omitted and in which spaced SMA film ribbons 102 are embedded. The polymer sheath 101 may be constructed of SMP material or other polymeric materials, and the SMA ribbons 102 may be composed of NiTiCu or other active materials. By way of example the SMA ribbons 102 may have a width of 10 microns to several millimeters and thickness of 0.1 to 10 microns, with the polymer sheath 101 having an external diameter of 0.1 to 10 mm and internal diameter of 0.05 to 9.9 mm In FIG. 15, the actuator or catheter wall section, generally indicted at 110 and is composed of an SMP tube 111 around which are wrapped SMA ribbons or wires 112. The materials of tube 111 and wires or ribbons may be constructed with parameters and of materials described above.

FIG. 16 is generally similar to FIG. 14 with the outer surface omitted to expose the SMA material, except the SMA material is in the form of a foil mesh retained against the polymer tube or member by a film support or anchor. The foil mesh may be embedded as in FIG. 14 or secured to the inner wall of the tube. As shown, the composite, generally indicated at 120 comprises a polymer sheath 121, SMA mesh ribbons 122 secured by film (ribbon) support/anchor 123. As in FIG. 14, the polymer sheath 121 may be constructed of SMP or other polymer materials, and the SMA mesh ribbons may have a thickness and width as in FIG. 14 embodiment.

FIG. 17 illustrates an overall catheter system which incorporates a plurality of composite SMA/SMP units, as in FIGS. 3A–3D mounted end to end, and with the SMA spring or coil in each unit of a different configuration for producing different degrees of change in diameter and length when activated, and with each SMA/SMP unit having an optical fiber therein for heating the shape memory material, the optical fibers being connected to a laser via a control mechanism. As shown, the catheter system generally indicated at 130 includes a catheter 131 operatively connected at its proximal end to a laser 132 via a light control mechanism, 133, and operatively connected at its distal end to a plurality of SMA/SMP units 134, 135 and 136 connected in series and form an extension of the catheter 131. While not shown, the SMA/SMP unit 136 may retain a coil stent, or medical device to be delivered at a selected location. Each of the SMA/SMP units 134–136 is provided with an optical fiber 137, 138 and 139 which extends through catheter 131 and operatively connected at the proximal end to laser 132 via light control mechanism 133, whereby light can be directed from laser 132 through any one of optical fibers 137–139 or all of optical fibers 137–139 for selectively activating SMA/SMP units 134–136. As in FIGS. 3A–3D, each of SMA/SMP units 134–136 include a coil or spring 140, 141 and 142, of SMA material which is embedded in a tube 143, 144, 145 or SMP material, with each unit having an opening 146, 147 and 148 with units 134–136 being interconnected by polymer members 149. Note that each of coils 140, 142 and 143 have been shown with different configurations to illustrate that each of the SMA/SMP units may be controlled differently to provide different functions when activated by laser light.

FIGS. 18A–18C illustrate an embodiment of an articulating catheter tip created by extruding processes in which the catheter lumen portion and the articulating tip each are provided with a plurality of longitudinally extending openings that are located off-axis (in the wall) of the catheter or tip. The tip indicated at 80 is a hollow SMP tube 81 approximately 1 mm in diameter (standard catheter size is 3 French), with, for example, 9 holes 82 and 3 slots 83 imbedded in the tube wall, see FIG. 18B. The tip (SMP tube) 80 mates up to the catheter lumen 84 that has 12 holes 85 embedded in the wall which contain, for example, power transmission fibers, see FIG. 18C. The distribution of these holes and slots are easily seen in FIGS. 18A–18C. Three laser light diffusers or heaters 86 are placed in holes 82 of tip 80 (see FIG. 18B) at 120 degrees apart and 60 degrees from the center of each extruded slot 83. Into the slots 83 are placed strips 87 of superelastic SMA that are annealed in a curled shape, as in FIG. 10A, thus a moment is applied to straighten them out. The three SMA strips 87 in their normal position act in equilibrium, thus holding the SMP tube 81 straight. While the strips 87 are stressed above a certain level, they experience incredible strains and are able to straighten under the load. When the load against strips 87 is relieved to a certain level, they recover all their strain in an attempt to "remember" their unreformed shape. Six of the holes 82, located a opposite ends of slots 83 are provided with power transmission fibers 88. Actuation is caused by selectively heating parts of the SMP tube 81 in which the SMA strips are imbedded. When SMP is heated above its glass transition temperature Tg, its elastic modulus decreases by a factor of about 200. Laser light is passed through only one diffuser 86, distributing the light into the SMP that is dyed to absorb specific wavelengths. This locally raises the temperature of the tube 81 above Tg and the polymer transforms, becoming 200 times less stiff. At this point, the tube 81 has an asymmetric moment of inertia, and the preloaded SMA strip 87 just opposite the powered diffuser 86 is acting against a lower effective spring constant. Asymetry allows this SMA strip to induce more curvature on the tube 81 than the other two strips 87 balance and the tube 81 bends. When light is removed from the diffuser 86, the SMP tube 81 stiffens into the new shape and the tube 81 remains bent. The tube 81 is straightened by powering all the diffusers 86 at once, allowing force equilibrium between the SMA strips 87 as the entire tube 81 is soft. The tube 81 is then cooled, regains its stiffness, and can be further maneuvered through the vessel. As seen in FIG. 18B, the catheter tip 80 shows a 120 degree radial offset between the SMA strips 87 and symmetric 120 degree radial offset between laser light diffusers 86, used as heaters. The 120 degree symmetric offsets lead to asymmetric moments while only one diffusers 86 is lit with the optical fiber laser and the tip 80 bends.

It has thus been shown that the present invention provides method and a group of biological bistable microelectromechanical devices, tools, or catheter wall sections, to aid in microsurgery. These bistable devices utilize shape memory material for producing a variable catheter modulous, a vibrational catheter, and inch-worm catheter, and a catheter with reversible fine positioning capabilities, reversible bending articulation of the distal tip, as well as controlled delivery, deployment and repositioning of objects such as a stent. The invention enables in vivo usage because the materials are biocompatible and convenient for intravascular use because of their enormous work output to volume ratio, as compared to existing microactuators.

While the present invention is particularly useful for vasculature and neurovasculature applications, particularly minimally invasive surgery, the devices may be used in non-medical applications such as nuclear techniques.

While various embodiments and operational procedures have been described, along with specific materials, parameters, etc., to exemplify and teach the principles of the invention such are not intended to be limiting. Modifications and changes may become apparent to those skilled in the art, and it is intended that the invention be limited only by the scope of the appended claim.

What is claimed is:

1. An apparatus for minimally invasive applications, said apparatus having a longitudinal axis with said apparatus extending in a radial direction from said longitudinal axis and said apparatus being activated by a change in temperature, comprising:
    a first unit comprising a first structure for at least positioning said apparatus, said first structure including a quantity of shape memory alloy and
    a second unit comprising a second structure for at least positioning said apparatus, said second structure including a quantity of shape memory polymer,
    said first unit comprising said first structure including said shape memory alloy having a longitudinally extending coiled configuration with more than one wrap, and
    said second unit comprising said second structure including said shape memory polymer comprising a cylinder,
    wherein said first unit is positioned in said second unit such that changes in temperature of said shape memory alloy causes said first unit to change position by a radial contraction and a longitudinal extension and to stretch said second unit comprising said second structure including said shape memory polymer along said longitudinal axis.

2. The apparatus of claim 1, wherein said first unit comprising said first structure including said shape memory alloy is embedded within second unit comprising said second structure including said shape memory polymer and wherein changes in temperature of said shape memory alloy causes said first unit to change position by a radial contraction and a longitudinal extension and to stretch said second unit comprising said second structure including said second shape memory polymer along said longitudinal axis.

3. The apparatus of claim 1, wherein said first unit comprising a first structure including a quantity of shape memory alloy comprises a coil configuration and wherein said second unit comprising said second structure including said shape memory polymer is a cylinder constructed so as to define a hollow tube cylinder with a wall and first unit comprising a first structure including a quantity of shape memory alloy that comprises said coil configuration is embedded in said wall.

4. The apparatus of claim 3, wherein said coil configuration of said first unit has an axis coaxial with said axis of said apparatus and said hollow tube cylinder of said second unit has an axis coaxial with said axis of said apparatus.

5. The improvement of claim 3, wherein said coil configuration has an axis off-set from an axis of said hollow tube.

6. The apparatus of claim 3, including a plurality of additional structures each having a longitudinally extending coiled configuration of shape memory alloy located within a shape memory polymer comprising a cylinder.

7. The improvement of claim 6, wherein each coil configuration has a different configuration.

8. The improvement of claim 6, wherein said plurality of structures are in a series configuration to said first structure and said second structure.

9. An apparatus for minimally invasive applications, said apparatus having a longitudinal axis with said apparatus extending in a radial direction from said longitudinal axis and said apparatus being activated by a change in temperature, comprising:
- a first structure for at least positioning said apparatus, said first structure having an axis aligned with said longitudinal axis of said apparatus and said first structure having a longitudinally extending coiled configuration with more than one wrap,
- said first structure including a quantity of shape memory alloy in said longitudinally extending coiled configuration with more than one wrap, and
- a second structure for at least positioning said apparatus,
- a quantity of shape memory polymer in said second structure,
- wherein said quantity of shape memory polymer in said second structure is a cylinder, and
- wherein said first structure including a quantity of shape memory alloy is positioned in said second structure that is a cylinder and wherein said first structure including a quantity of shape memory alloy is positioned in said second structure that is a cylinder such that changes in temperature of said shape memory alloy causes said first structure to change position by a radial contraction and a longitudinal extension and to stretch said second structure along said longitudinal axis.

10. The apparatus of claim 9, wherein said quantity of shape memory alloy has a ribbon configuration.

11. The improvement of claim 1, wherein said quantity of shape memory alloy is composed of NiTiCu.

12. The apparatus of claim 9, wherein said quantity of shape memory alloy is composed of a plurality of shape memory alloy strips.

13. The apparatus of claim 9, wherein said quantity of cylindrical shape memory polymer has a closed cylinder configuration.

14. The apparatus of claim 13, wherein said quantity of shape memory alloy has a coiled spring configuration located within said shape memory polymer.

15. The apparatus of claim 13, wherein said quantity of shape memory alloy is composed of a plurality of strips, and wherein said strips are located in a wall surface of said shape polymer.

16. The apparatus of claim 13, wherein said quantity of shape memory alloy is composed of a plurality of sections embedded in said shape memory polymer.

17. The improvement of claim 13, wherein said quantity of shape memory alloy is composed of net-like configuration attached to said tubular configuration.

18. The improvement of claim 13, wherein said quantity of shape memory alloy is composed of a compressed spring located in a wall surface of tubular configuration.

19. The improvement of claim 13, wherein said quantity of shape alloy is composed of a plurality of bent sections located in openings said tubular configuration.

20. The improvement of claim 13, wherein said quantity of shape memory alloy is composed of a plurality of ribbons mounted in spaced relation around said tubular configuration.

21. The improvement of claim 14, wherein said plurality of ribbons are of mesh configuration and mounted to a said tubular configuration support members.

22. The apparatus of claim 9, wherein said quantity of shape memory alloy has a coiled spring configuration, wherein said quantity of shape memory polymer is a cylinder and wherein said coiled spring configuration is embedded in said shape memory polymer.

23. The improvement of claim 1, wherein said quantity of shape memory alloy comprises a plurality of strips, wherein said quantity of shape memory polymer is a tubular configuration and includes a plurality of longitudinally extending openings and a plurality of longitudinal slots, wherein said plurality of strips are located in said plurality of longitudinally extending slots.

24. The improvement of claim 23, additionally including a plurality of light diffusers mounted in certain of said longitudinally extending openings.

25. The improvement of claim 23, wherein said tubular configuration is constructed to mate up to a catheter having a plurality of longitudinally extending openings, whereby said slots and openings in said tubular configuration align with said openings in said catheter.

26. The improvement of claim 9, including a light source connected to said apparatus via a plurality of optical fibers and light control mechanism.

27. The apparatus of claim 26, wherein said light source is a laser.

28. An articulated tip for a catheter, said articulated tip having a central axis with said articulated tip extending in a radial direction from said central axis and said articulated tip being activated by a change in temperature, comprising
- a composite of shape memory alloy forming a first portion of said articulated tip with said composite of shape memory alloy having an axis that is aligned with said central axis of the articulated tip for a catheter
- and shape memory polymer forming a second portion of said articulated tip, wherein said shape memory polymer comprises a cylinder, and wherein said first portion of said articulated tip with said composite of shape memory alloy is positioned in second portion of said articulated tip such that changes in temperature of said shape memory alloy causes said first portion of said articulated tip with said composite of shape memory alloy to change position by a radial contraction and a longitudinal extension and to stretch said second portion of said articulated along said central axis.

29. A device for reversible fine positioning of an object, said device being activated by a change in temperature, comprising:
- a member constructed of shape memory polymer portion, wherein said shape memory polymer portion comprises a cylinder and said cylinder has a cylinder central axis,
- said member including a shape memory alloy portion with a coiled configuration with more than one wrap, wherein said shape memory alloy portion is located in said shape memory polymer portion such that changes in temperature of said shape memory alloy portion causes said shape memory alloy portion to change position by a radial contraction and a longitudinal extension and to stretch said shape memory polymer portion along said cylinder central axis that will cause said device to move upon a change in configuration of said shape memory alloy portion, and
- means for selectively heating said shape memory alloy portion to change temperature of said shape memory alloy portion causing said shape memory alloy portion to change position by a radial contraction and a longitudinal extension and to stretch said shape memory polymer portion along said cylinder central axis and cause a change in configuration thereof, whereby the change in configuration results in positioning of said object.

* * * * *